US011813007B2

(12) United States Patent
Heino et al.

(10) Patent No.: US 11,813,007 B2
(45) Date of Patent: Nov. 14, 2023

(54) ORTHOPEDIC BIOABSORBABLE IMPLANTS

(71) Applicant: ARCTIC BIOMATERIALS OY, Tampere (FI)

(72) Inventors: Harri Heino, Tampere (FI); Timo Lehtonen, Tampere (FI); Mikko Huttunen, Tampere (FI); Miika Lehtola, Tampere (FI)

(73) Assignee: ARCTIC BIOMATERIALS OY, Tampere (FI)

( * ) Notice: Subject to any disclaimer, the term of this patent is extended or adjusted under 35 U.S.C. 154(b) by 363 days.

(21) Appl. No.: 16/756,271

(22) PCT Filed: Oct. 15, 2018

(86) PCT No.: PCT/EP2018/078007
§ 371 (c)(1),
(2) Date: Apr. 15, 2020

(87) PCT Pub. No.: WO2019/076788
PCT Pub. Date: Apr. 25, 2019

(65) Prior Publication Data
US 2020/0323573 A1    Oct. 15, 2020

(30) Foreign Application Priority Data
Oct. 16, 2017   (EP) .................................. 17196561

(51) Int. Cl.
*A61B 17/80*   (2006.01)
*A61L 31/02*   (2006.01)
(Continued)

(52) U.S. Cl.
CPC ........ *A61B 17/8061* (2013.01); *A61L 31/026* (2013.01); *A61L 31/124* (2013.01);
(Continued)

(58) Field of Classification Search
CPC .................. A61B 17/8061; A61B 2017/00004
See application file for complete search history.

(56) References Cited

U.S. PATENT DOCUMENTS

| 5,294,391 A | 3/1994 | McMillin |
| 2006/0041262 A1* | 2/2006 | Calvert .................. A61L 27/04 |
| | | 606/76 |

(Continued)

FOREIGN PATENT DOCUMENTS

| CN | 101594831 | 12/2009 |
| CN | 105641751 | 6/2016 |

(Continued)

OTHER PUBLICATIONS

Office Action dated Jun. 22, 2021 in corresponding Japanese Application No. 2020-542189 (with translation), 10 pages.
(Continued)

*Primary Examiner* — Olivia C Chang
(74) *Attorney, Agent, or Firm* — Nixon & Vanderhye PC (57) ABSTRACT

The present invention provides an orthopedic implant comprising a continuous reinforced composite filament in a freely predetermined fiber orientation in multiple continuous successive layers, wherein the continuous reinforced composite filament comprises a bioabsorbable polymer matrix and a continuous bioabsorbable reinforcing fiber or fiber bundle, and whereby the continuous bioabsorbable reinforcing fiber or fiber bundle of consecutive layers at least partly intermingles and/or intertwines forming a three dimensionally interlocked continuous fiber structure.

26 Claims, 9 Drawing Sheets (51) Int. Cl.
*A61L 31/12* (2006.01)
*A61L 31/14* (2006.01)
*A61B 17/00* (2006.01)
*A61B 17/56* (2006.01)

(52) U.S. Cl.
CPC ... *A61L 31/148* (2013.01); *A61B 2017/00004* (2013.01); *A61B 2017/00526* (2013.01); *A61B 2017/564* (2013.01)

(56) References Cited

U.S. PATENT DOCUMENTS

| | | |
|---|---|---|
| 2007/0141111 A1 | 6/2007 | Suokas et al. |
| 2014/0235754 A1 | 8/2014 | Rose et al. |
| 2017/0173868 A1 | 6/2017 | Mark |

FOREIGN PATENT DOCUMENTS

| | | |
|---|---|---|
| FI | 20031174 | 8/2003 |
| JP | 09-502999 | 3/1997 |
| JP | 2004-160157 | 6/2004 |
| JP | 2010-511751 | 4/2010 |
| JP | 2015-006514 | 1/2015 |
| JP | 2016-517319 | 6/2016 |
| KR | 10-2014-0014354 | 2/2014 |
| KR | 10-2017-0051409 | 5/2017 |
| KR | 10-2017-0098846 | 8/2017 |
| WO | 2008/067531 | 6/2008 |
| WO | 2010/122019 | 10/2010 |
| WO | 2010/128039 | 11/2010 |
| WO | 2014/153535 | 9/2014 |
| WO | 2016/035088 | 3/2016 |
| WO | 2016/103049 | 6/2016 |
| WO | 2017/123726 | 7/2017 |

OTHER PUBLICATIONS

International Search Report and Written Opinion of the ISA for PCT/EP2018/078007 dated Jan. 18, 2019, 13 pages.
International Preliminary Report on Patentability for PCT/EP2018/078007 completed Aug. 26, 2019, 6 pages.
Extended EP Search Report for 17196561.9 dated Apr. 30, 2018, 8 pages.
Matsuzaki et al., "Three-dimensional printing of continuous-fiber composites by in-nozzle impregnation", Scientific Reports, vol. 6, No. 1, Mar. 11, 2016, 7 pages.
Notice of Opposition dated Jan. 4, 2022 in corresponding European Application No. 17196561.9, 19 pages.
Williams, "The Williams Dictionary of Biomaterials" Liverpool University Press, 364 pages (1999).
Office Action dated Aug. 18, 2021 in Chinese Application No. 201880079363.5 (with English-language translation), 14 pages.
Decision for Grant of Patent dated Oct. 4, 2022 in corresponding Korean Application No. 10-2020-7013750 (with translation), 5 pages.

* cited by examiner

Figure 9

ORTHOPEDIC BIOABSORBABLE IMPLANTS

This application is the U.S. national phase of International Application No. PCT/EP2018/078007 filed Oct. 15, 2018 which designated the U.S. and claims priority to EP Patent Application No. 17196561.9 filed Oct. 16, 2017, the entire contents of each of which are hereby incorporated by reference.

FIELD OF THE INVENTION

The present invention relates to orthopedic implants manufactured from a continuous reinforced composite filament comprising a bioabsorbable polymer matrix and a continuous bioabsorbable fiber or fiber bundle and to a process of manufacturing an orthopedic implant from a continuous reinforced composite filament comprising a bioabsorbable polymer matrix and a continuous bioabsorbable fiber or fiber bundle.

BACKGROUND OF THE INVENTION

To avoid use of metallic implants for internal fixation in orthopedic trauma and reconstruction surgery bioabsorbable implants typically made of lactide based polymers have been studied and applied in clinical use since the mid 1980's. However, the mechanical properties of lactide based polymer materials as such are not very good. They are relatively weak and brittle compared to metal alloys typically used in orthopedic implants. Ceramic particles, typically hydroxyampatites and tricalciumphosphates (TCP), e.g. β-TCP, have been added to the polymer matrix to improve the biocompatibility and bone ingrowth during the degradation of the implant material. These composite materials, however, have rather worse than better mechanical properties compared to implants made of pure polymer.

Bioabsorbable glass materials have been successfully used as a bone filler material since late 1960's as granules or blocks. Glass is brittle and thus not well suitable as fixation implant material as such. However, some of bioabsorbable silica based glass materials can also be drawn into thin glass fibers with a tensile strength around 2000 MPa. Combining these glass fibers with bioabsorbable polymers can create strong reinforced bioabsorbable composite materials having superior properties. The strength is close to that of metal materials, but the material is still bioabsorbable. Moreover, these types of glasses have been shown to be beneficial for new bone formation and possessing antimicrobial properties.

Characteristic for fiber composite materials is high strength along the fiber direction and low strength perpendicular to the fiber. That sets a challenge for providing a method for controlling the fiber orientation in the product and thus its strength.

Typical manufacturing techniques for manufacturing composite products from this type of thermoplastic glass fiber composite materials are injection molding and compression molding.

In the injection molding process pellets containing polymer and glass fiber are fed into a dosing unit of an injection molding machine. They are melted and chopped in the process and therefore it is challenging to retain long enough fibers for good reinforcing effect in the final product. Moreover, the fiber orientation is only controlled by the material flow in the mold during the injection. It is difficult to ensure that the fiber orientation is always optimal for the stresses the implant is designed for.

In traditional compression molding techniques fiber structures are laid into a mold as preforms that typically consist of woven structures having standard fiber angles. Preparation of the preforms is burdensome. Typically it is manual work consisting of cutting, shaping and stacking. With this method it is also difficult to tailor the fiber orientation of specific areas of the implant to adapt the product to the requirements of the application.

BRIEF DESCRIPTION OF THE INVENTION

An object of the present invention is thus to provide an orthopedic implant and a process for manufacturing an orthopedic implant so as to overcome the above problems. The objects of the invention are achieved by a process and an orthopedic implant, which are characterized by what is stated in the independent claims. The preferred embodiments of the invention are disclosed in the dependent claims.

The invention is based on the idea of enabling free defining of desired fiber orientation in the implant layer by layer. This is achieved by depositing a continuous reinforced composite filament comprising a bioabsorbable polymer matrix, and a continuous bioabsorbable fiber or fiber bundle by a three dimensionally controlled fiber strand feeding machine (e.g. 3D printer) in a predetermined fiber orientation in continuous successive layers. This forms a filament preform comprising the continuous bioabsorbable reinforcing fiber or fiber bundle in multiple continuous successive layers. Advantageously molding the filament preform to final shape of the orthopedic implant forces the continuous bioabsorbable reinforcing fiber or fiber bundle to at least partly intermingle and/or intertwine under heat and pressure thus forming a three dimensionally interlocked continuous fiber structure.

BRIEF DESCRIPTION OF THE DRAWINGS

In the following the invention will be described in greater detail by means of preferred embodiments with reference to the attached [accompanying] drawings, in which.

DETAILED DESCRIPTION OF THE INVENTION

The present invention provides an orthopedic implant comprising a continuous reinforced composite filament in a freely predetermined fiber orientation in multiple continuous successive layers, wherein the continuous reinforced composite filament comprises a bioabsorbable polymer matrix and a continuous bioabsorbable reinforcing fiber or fiber bundle, and whereby the continuous bioabsorbable reinforcing fiber or fiber bundle of consecutive layers at least partly intermingles and/or intertwines forming a three dimensionally interlocked continuous fiber structure.

The terms used in this application, if not otherwise defined, are those agreed on at the consensus conference on biomaterials in 1987 and 1992, see Williams, DF (ed.): Definitions in biomaterials: Proceedings of a consensus conference of the European Society for Biomaterials, Chester, England. Mar. 3-5, 1986. Elsevier, Amsterdam 1987, and Williams D F, Black J, Doherty P J. Second consensus conference on definitions in biomaterials. In: Doherty P J, Williams R L, Williams D F, Lee A J (eds). Biomaterial-Tissue Interfaces. Amsterdam: Elsevier, 1992.

Herein and hereafter "optional" or "optionally" denotes that the subsequently described event or circumstance may but need not occur, and that the description includes instances where the event or circumstance occurs and instances in which it does not. "Comprises" or "comprising" denotes that the subsequently described set may but need not include other elements.

The orthopedic implant of the present invention comprises a continuous reinforced composite filament i.e. a bioabsorbable filament that comprises a bioabsorbable polymer matrix and a continuous bioabsorbable reinforcing fiber or fiber bundle to increase the mechanical strength of the bioabsorbable polymer.

The term "continuous reinforced composite filament" refers to a filament that has at least the length of the maximum dimension of the end product. Preferably the length of continuous reinforced composite filament is at least 2 to 10 times the maximum dimension of the end product. Most preferably the length of continuous reinforced composite filament is such that only one strand of the filament is required for forming the end product as strength of the end product is proportional to the length of the continuous bioabsorbable reinforcing fiber.

The term "filament" refers to any suitable depositable structure comprising the bioabsorbable polymer matrix and the continuous bioabsorbable reinforcing fiber or fiber bundle as the core of the structure. The filament may thus for example be spherical (e.g. strand or rod) or planar (e.g. tape). Preferably the filament is spherical.

The weight ratio of the continuous bioabsorbable reinforcing fiber or fiber bundle to the bioabsorbable polymer is preferably such that the continuous bioabsorbable reinforcing fiber content is 10 to 90 weight % of the total weight of the reinforced composite filament, preferably 20 to 80 wt %, more preferably from 30 to 70 wt % and most preferably 40 to 60 wt %.

The smallest dimension of the continuous reinforced composite filament is preferably from 0.05 mm to 20 mm, more preferably from 0.5 mm to 3.0 mm, most preferably from 0.8 mm to 2.0 mm.

When the continuous reinforced composite filament is in the form of a spherical continuous reinforced composite filament the average filament diameter of the continuous reinforced composite filament is preferably from 0.5 mm to 3.0 mm, more preferably from 0.8 mm to 2.0 mm. The large filament diameter enhances intermingling and/or intertwining of the continuous bioabsorbable reinforcing fiber or fiber bundle of consecutive layers and makes the fiber laying process faster.

The term "bioabsorbable" refers to material which in contact with biological tissues and/or physiological fluids will, following implantation, degrade, resorb and/or absorb into the body while maintaining its mechanical properties for a certain period of time. Accordingly e.g. term "bioresorbable" may be used interchangeably with the term "bioabsorbable".

The bioabsorbable polymer of the present invention may be a homopolymer or a copolymer, including random copolymer, block copolymer, or graft copolymer. Further, the bioabsorbable polymer may be a linear polymer, a branched polymer, or a dendrimer. The bioabsorbable polymers may be of natural or synthetic origin.

In accordance with the present invention the following absorbable polymers, copolymers and terpolymers may be used as suitable bioabsorbable polymers. For example, polylactides (PLA), poly-L-lactide (PLLA), poly-DL-lactide (PDLLA); polyglycolide (PGA); copolymers of glycolide, glycolide/trimethylene carbonate copolymers (PGA/TMC); other copolymers of PLA, such as lactide/tetramethylglycolide copolymers, lactide/trimethylene carbonate copolymers, lactide/d-valerolactone copolymers, lactide/ε-caprolactone copolymers, L-lactide/DL-lactide copolymers, glycolide/L-lactide copolymers (PGA/PLLA), polylactide-co-glycolide; terpolymers of PLA, such as lactide/glycolide/trimethylene carbonate terpolymers, lactide/glycolide/ε-caprolactone terpolymers, PLA/polyethylene oxide copolymers; polydepsipeptides; unsymmetrically 3,6-substituted poly-1,4-dioxane-2,5-diones; polyhydroxyalkanoates, such as polyhydroxybutyrates (PHB); PHB/b-hydroxyvalerate copolymers (PHB/PHV); poly-b-hydroxypropionate (PHPA); poly-p-dioxanone (PDS); poly-d-valerolactone-poly-ε-caprolactone, poly(ε-caprolactone-DL-lactide) copolymers; methylmethacrylate-N-vinyl pyrrolidone copolymers; polyesteramides; polyesters of oxalic acid; polydihydropyrans; polyalkyl-2-cyanoacrylates; polyurethanes (PU); polyvinylalcohol (PVA); polypeptides; poly-b-malic acid (PMLA); poly-b-alkanoic acids; polycarbonates; polyorthoesters; polyphosphates; poly(ester anhydrides); and mixtures thereof; and natural polymers, such as sugars, starch, cellulose and cellulose derivatives, polysaccharides, collagen, chitosan, fibrin, hyaluronic acid, polypeptides and proteins. Mixtures of any of the above-mentioned polymers and their various forms may also be used.

Particular examples of suitable bioabsorbable polymers include, but are not limited to, polymers made from lactide, glycolide, caprolactone, valerolactone, carbonates, dioxanones, δ-valerolactone, 1,dioxepanones, ethylene glycol, ethylene oxide, esteramides, γ-hydroxyvalerate, β-hydroxypropionate, alpha-hydroxy acid, hydroxybuterates, polyorthoesters, hydroxy alkanoates, tyrosine carbonates, polyimide carbonates, polyimino carbonates, polyurethanes, polyanhydrides, and copolymers and any combinations thereof. Suitable natural biodegradable polymers include collagen, chitin, chitosan, cellulose, polyaminoacids, polysaccharides, and copolymers, derivatives and combinations thereof.

The bioabsorbable polymer is preferably selected from the group consisting of bioabsorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof.

In addition to the bioabsorbable polymer matrix the continuous reinforced composite filament comprises a continuous bioabsorbable reinforcing fiber or fiber bundle i.e. multiple parallel strands of said continuous bioabsorbable reinforcing fiber.

The average fiber diameter of a single continuous reinforcing fiber is typically from 1 to 35 μm, preferably from 5 to 30 μm, more preferably from 10 to 15 μm.

The continuous reinforcing fiber or fiber bundle may be comprised of organic or inorganic material. The continuous reinforcing fiber may be comprised of a biodegradable glass or glass-like materials, a ceramic, a mineral composition such as hydroxyapatite, tricalcium phosphate, calcium sulfate or calcium phosphate, a cellulosic material, or any other continuous fiber known in the art to increase the mechanical properties of a bioabsorbable polymer. The continuous reinforcing fiber may also be a bioabsorbable polymer itself. Preferably, the continuous reinforcing fiber is comprised of a bioabsorbable glass, ceramic, or mineral composition, in particular of a bioabsorbable glass.

In a preferred example, the continuous bioabsorbable reinforcing fiber or fiber bundle is comprised of silica-based mineral compound i.e. the continuous bioabsorbable reinforcing fiber is a bioabsorbable glass fiber. Most preferably the continuous bioabsorbable reinforcing fiber or fiber bundle is a melt derived bioabsorbable glass fiber.

The melt derived bioabsorbable glass fiber may have composition in the following weight % ranges (as a percent over the total weight of the glass fiber composition):

| | |
|---|---|
| $SiO_2$ | 40 to 90 wt %, |
| $Na_2O$ | 5 to 30 wt %, |
| $K_2O$ | 0 to 20 wt %, |
| CaO | 5 to 30 wt %, |
| MgO | 0 to 10 wt %, |
| $P_2O_5$ | 0 to 10 mol %, |
| $B_2O_3$ | 0 to 15 wt %, |
| $Al_2O_3$ | 0 to 5 wt %, |
| $CaF_3$ | 0 to 25 wt %, |
| SrO | 0 to 10 wt %, and |
| $Li_2O$ | 0 to 1 wt %. |

In a first example the melt derived bioabsorbable glass fiber has composition in the following mol % ranges:

| | |
|---|---|
| $SiO_2$ | 50 to 75 wt %, |
| $Na_2O$ | 5 to 20 wt %, |
| $K_2O$ | 0 to 10 wt %, |
| CaO | 5 to 25 wt %, |
| MgO | 0 to 10 wt %, |
| $P_2O_5$ | 0.5 to 5 wt %, |
| $B_2O_3$ | 0 to 15 wt %, |
| $Al_2O_3$ | 0 to 5 wt %, and |
| SrO | 0 to 5 wt %. |

In a second example the melt derived bioabsorbable glass fiber has composition in the following weight % ranges:

| | |
|---|---|
| $SiO_2$ | 60 to 72 wt %, |
| $Na_2O$ | 10 to 20 wt %, |
| $K_2O$ | 0.1 to 10 wt %, |
| CaO | 5 to 15 wt %, |
| MgO | 1 to 10 wt %, |
| $P_2O_5$ | 0.5 to 2 wt %, |
| SrO | 0 to 3 wt %, and |
| $B_2O_3$ | 0 to 10 wt %. |

In an advantageous example the continuous reinforced composite filament comprises a bioabsorbable polymer is preferably selected from the group consisting of bioabsorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof; and a continuous bioabsorbable reinforcing fiber or fiber bundle comprised of a melt derived bioabsorbable glass fiber. Preferably the composition of the melt derived bioabsorbable glass fiber is as defined above.

In addition to polymer matrix and the continuous bioabsorbable reinforcing fiber or fiber bundle, the continuous reinforced composite filament may also comprise a compatibilizer for binding the bioabsorbable polymer to the continuous reinforcing fiber or fiber bundle.

Additionally or alternatively the continuous reinforced composite filament may also comprise one or more filler materials, such as ceramic particles (e.g. tricalciumphosphate particles).

The term "freely predetermined fiber orientation" refers to unrestricted choice of fiber orientation of the continuous bioabsorbable reinforcing fiber or fiber bundle of the continuous reinforced composite filament when designing the desired fiber orientation of the orthopedic implant. The desired fiber orientation, however, may be dependent of the requirements of the application.

The term "multiple continuous successive layers" refers to successive layers of continuous reinforced composite filament wherein the continuous bioabsorbable reinforcing fiber or fiber bundle continues unbroken at least from one filament layer to the next.

The term "intermingles and/or intertwines" refers to merging of successive filament layers formed of the continuous reinforced composite filament during the manufacture of the orthopedic implant so that the continuous bioabsorbable reinforcing fiber or fiber bundle of different layers intermixes and/or twists in the final implant product thus forming "a three dimensionally interlocked continuous fiber structure". This may be achieved either by the predesign of the fiber orientation and/or the filament layer overlap of the filament preform or by compression molding of the filament preform as discussed below or both.

Examples of orthopedic implants of the present invention include bone fixation plates, pins, screws, tacks, nails, meshes, stents and anchors. These orthopedic implants are mainly used for bone to bone, soft tissue to bone or soft tissue to soft tissue fixation in order to maintain desired alignment of the healing tissues until they are again ready to carry the physiological loads acting in the implantation area. Being bioabsorbable, these implants degrade in the human body conditions and their degradation products are absorbed and metabolized by the body.

Further the present invention provides a process for manufacturing an orthopedic implant, comprising (a) depositing a continuous reinforced composite filament comprising a bioabsorbable polymer matrix and a continuous bioabsorbable fiber or fiber bundle by a three dimensionally controlled fiber placement device, such as a fiber strand feeding machine (e.g. 3D printer), in a freely predetermined fiber orientation in continuous successive layers to form a filament preform, and (b) molding the filament preform in a mold to obtain a molded product having final shape of the orthopedic implant.

The fiber orientation may be freely predetermined for example by software that enables drawing of the desired fiber orientation for the orthopedic implant layer by layer. In one example of the present process, the continuous reinforced composite filament structure is defined layer by layer using free drawing with a software. In another example of the present process, the continuous reinforced composite filament structure is defined layer by layer using combination of free drawing and computer calculation with a software. In still further example of the present process, the continuous reinforced composite filament structure is defined layer by layer using computer calculation with a software.

Figure 1:
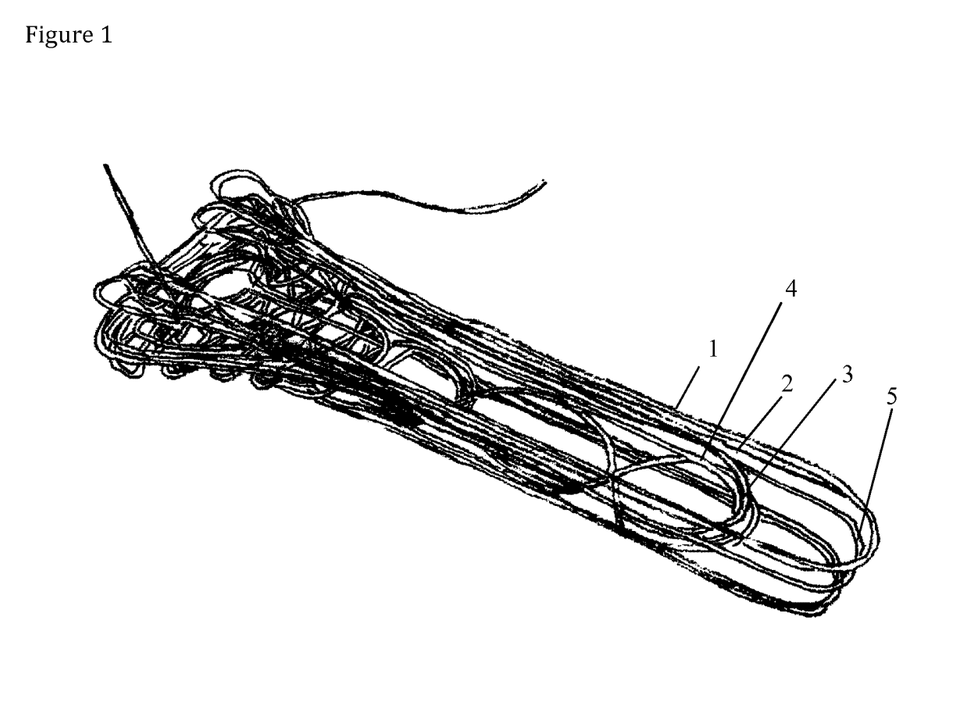
FIG. 1 illustrates designing fiber orientation layer by layer with an orientation designing software.

FIG. 1 illustrates designing fiber orientation layer by layer with an orientation designing software. With reference to FIG. 1, a continuous line is drawn where the continuous reinforced composite filament is desired to be placed in the filament preform. After completing one layer (1) moving to next layer (2, 3, 4, etc.) allows continuing drawing. After completing the drawing the software generates a code defining the fiber route. The code defines the X-Y-Z coordinates of the reinforced composite filament. The code may be for example a G-code, typically used in CNC machines to control the movements of the machining head or in 3D printer to control the movement of the printing head. It consists of X-Y-Z coordinates and in this case a filament extrusion value. This code is then fed to the three dimensionally controlled fiber placement device, which heats up the continuous reinforced composite filament and extrudes it along the route defined by drawing layer by layer thus forming a filament preform comprising multiple filament layers.

Figure 2:
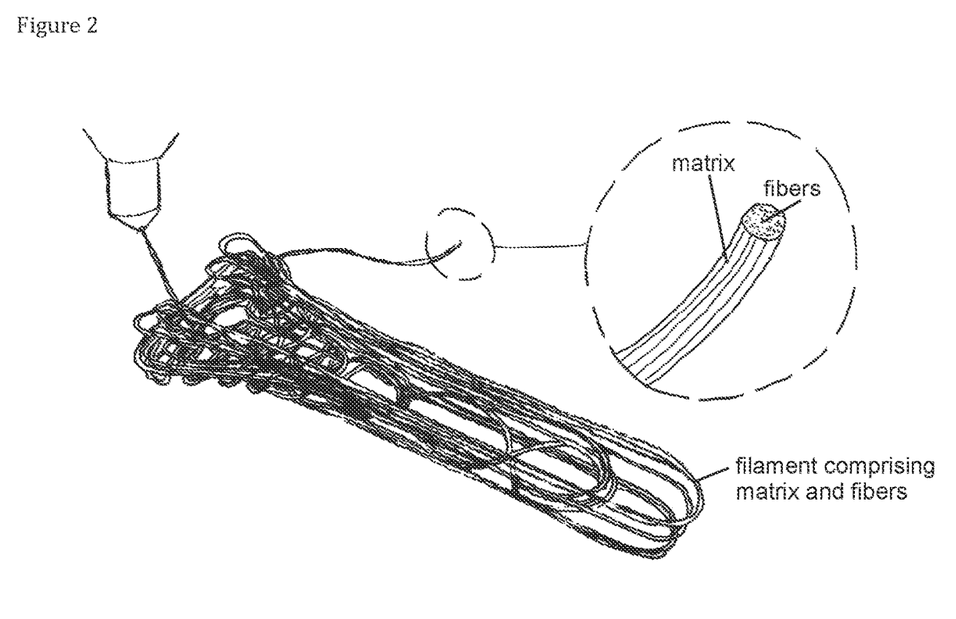
FIG. 2 shows printing of an illustrative example of a filament preform.

An illustrative example of a filament preform is shown in FIG. 2. Typically the filament preform comprises 2 to 200 filament layers, preferably from 2 to 20, more preferably from 2 to 10, most preferably from 2 to 6. Each filament layer may be aligned in a different direction or some of the filament layers may be aligned in the same direction as the other filament layers. When the implant comprises one or more hole(s), said hole(s) is(are) preferably encircled at least once, more preferably 2 to 3 times, by the continuous reinforced composite filament. Typically the thickness of the filament layers varies from 0.05 mm to 3.5 mm. Preferably the filament layers are 0.5 to 3.0 mm in thickness and more preferably 0.8 to 2.0 mm. The thickness of the filament layers is directly dependent on the thickness of the reinforced composite filament.

In accordance with the present process, after obtaining the filament preform, it is then molded to obtain a molded product having final shape of the orthopedic implant. Advantageously compression molding forces the continuous bioabsorbable reinforcing fiber or fiber bundle to at least partly intermingle and/or intertwine under heat and pressure as the bioabsorbable polymer matrix melts under the molding conditions thus forming a three dimensionally interlocked continuous fiber structure of the solid orthopedic implant.

Figure 3:
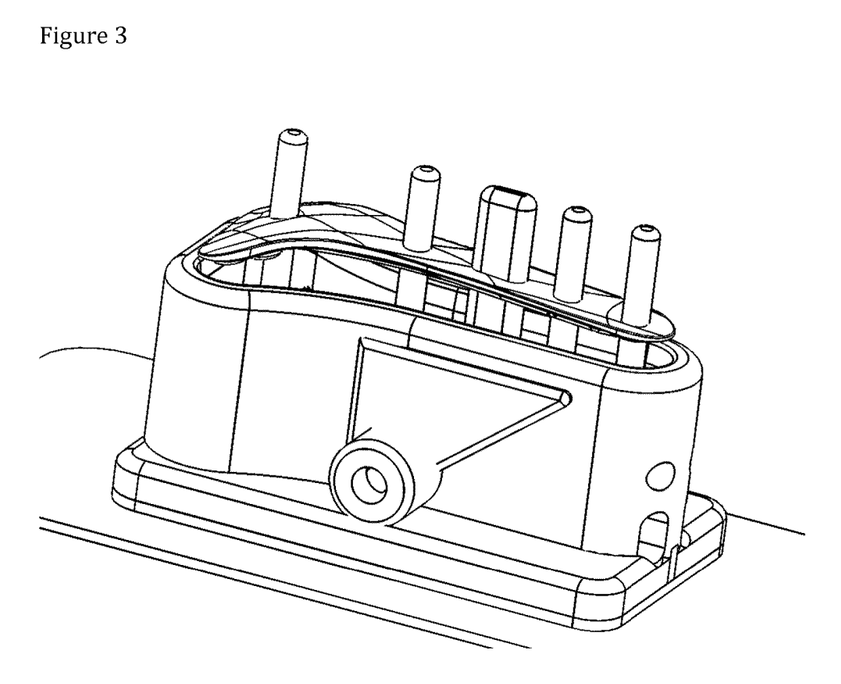
FIG. 3 shows a freshly compression molded implant.

Molding of the filament preform may be achieved by different molding techniques in a mold to obtain a molded product having final shape of the orthopedic implant. Advantageously the filament preform is compression molded in a mold to obtain a molded product having final shape of the orthopedic implant. Compression molding of the filament preform ensures that the continuous bioabsorbable reinforcing fiber or fiber bundle at least partly intermingles and/or intertwines forming a three dimensionally interlocked continuous fiber structure. FIG. 3 shows a freshly compression molded implant.

The mold may have curved shape, one or more holes and/or three dimensional features on any of the surfaces. Mold structures may have moving cores and ejectors to enable fully automated manufacturing of the here contemplated orthopedic implants.

Optionally the process further comprises surface finishing of the molded product. Preferably the surface finishing is TCP blasting of the molded product. This ensures optimal tissue response.

Figure 4:
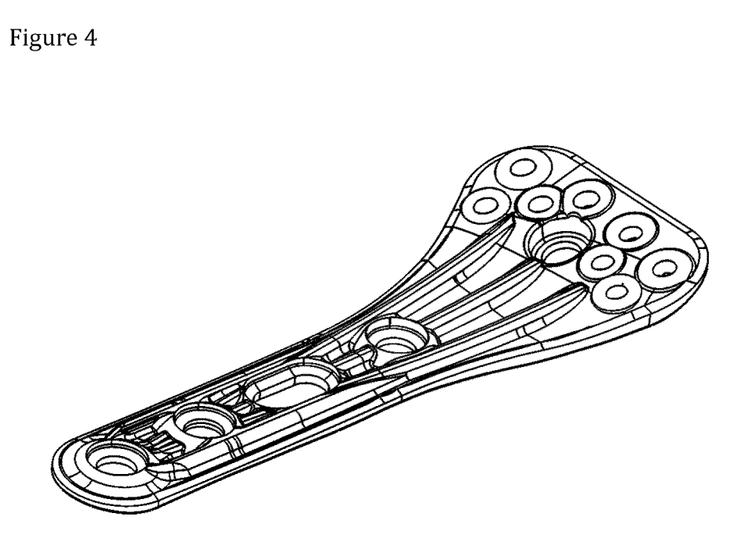
FIG. 4 shows a compression molded distal radius plate.

FIGS. 1 to 4 illustrate key stages of the present process. FIG. 1 shows a designed G-code route of the freely predetermined fiber orientation of the filament preform; FIG. 2 shows a fully deposited filament preform; FIG. 3 shows a result of compression molding of the filament preform; and FIG. 4 shows a compression molded product utilizable as a distal radius plate.

Figure 5:
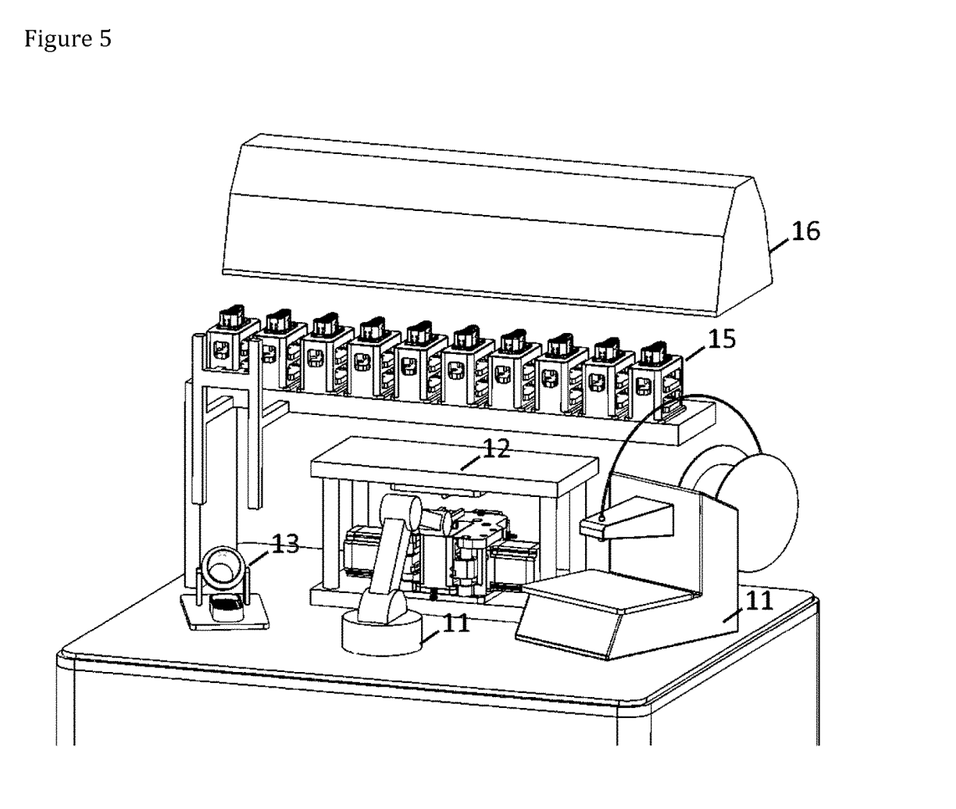
FIG. 5 shows a schematic view of an automatic production module.

The whole production process of the present orthopedic implants may be fitted into a very small compact production module, which can autonomously prepare various product types in desired quantities. FIG. 5 shows a schematic view of an example of an automatic production module. The module comprises inside of a module processing space (not shown) a 3D printer (11) for printing the filament preforms, a compression molding unit (12) comprising a press for compression molding, a finishing unit (13) for automatic surface finishing of the molded product and a robot (14) for moving the preforms and molded and final products. The module may also comprise a mold storage, where a robot or a separate manipulator can place the molds that are not currently in use in the press. The exemplary automatic production model shown in FIG. 5 comprises an automatic 10 mold changer system (15). The inside of the module processing space is advantageously a controlled environment, typically selected from a group consisting of cleanroom, sterile, aseptic, humidity controlled, shield gas, sterilization gas environments. With reference to FIG. 5, the exemplary automatic production model comprises an air filter and dryer unit (16). The whole production module preferably has a footprint of about 1 m$^2$, but it may also be larger or smaller than that.

In an embodiment, a continuous reinforced composite filament comprising a bioabsorbable polymer matrix and continuous bioabsorbable reinforcing glass fiber is used such that a freely configurable intermingled continuous fiber structure is formed. Thereby an orthopedic implant having an intermingled continuous fiber structure is obtainable. The obtained orthopedic implant is bioabsorbable and has improved strength properties.

In an embodiment, a continuous reinforced composite filament comprising a bioabsorbable polymer matrix and continuous bioabsorbable reinforcing glass fiber is used, wherein the glass fiber has a tensile strength of about 2000 MPa. This enables obtaining a composite tensile strength of more than 450 MPa, and a composite flexural strength of more than 650 MPa. Thereby an orthopedic implant having composite tensile strength of more than 450 MPa, and a composite flexural strength of more than 650 MPa, is obtained.

In an embodiment, the intermingled continuous fiber structure of the orthopedic implant is obtained by pressing in a mold. That way the structure of the orthopedic implant is dense, and the continuous bioabsorbable reinforcing fiber or fiber bundle of consecutive layers at least partly intermingles and/or intertwines forming a three dimensionally interlocked continuous fiber structure. A 3D printer may be used to make a fiber composite skeleton or preform which is then pressed in the mold to get the final shape of the orthopedic implant. That way dense composite material and a strongly intermingled structure between the layers are obtained. Thereby a composite structure of the orthopedic implant having enhanced strength properties is achieved. The exact shape of the orthopedic implant is defined by the mold.

The preform is porous and has a lot of empty space in each layer. Therefore, the preform is a lot thicker (larger) than the final molded product. Thus, when the preform is pressure molded into the final form, an interlaced fibrous structure is created, which effectively blocks delamination.

EXAMPLES

Example 1

Fiber orientation of four layers was designed by free drawing using a software. Four layer preforms were made based on the G-code generated by the fiber design software using a 3D printer and continuous 1.7 mm thick fiber strand. Preforms were placed into a mold at 175° C. and mold was partially closed for preheating for 60 seconds. Then the mold was closed and pressure was applied for 30 seconds. Pressure was kept on and mold was cooled down to room temperature before opening the mold and ejection of the parts. The mold size was 30×80 mm and the thickness of the sample plates was 2 mm.

Three different samples were made. Sample 1 had longitudinal fiber orientation in all the four layers. Sample 2 had longitudinal fiber orientation in top and bottom layers and +45° and −45° fiber orientation in the two middle layers. In addition to these three samples types a reference sample 3 were made out of similar polymer with ceramic particle filler. This sample was made by placing the ceramic containing polymer pellets into the mold and compression molding of the plates with a similar process as was used for manufacturing of the fiber containing samples.

The test specimen were cut longitudinally from the middle of the plates to gain pure fiber orientation for testing without turning loops at the sides of the sample.

FIGS. 6a and 6b shows results of mechanical tests of four implant samples.

Figure 6:
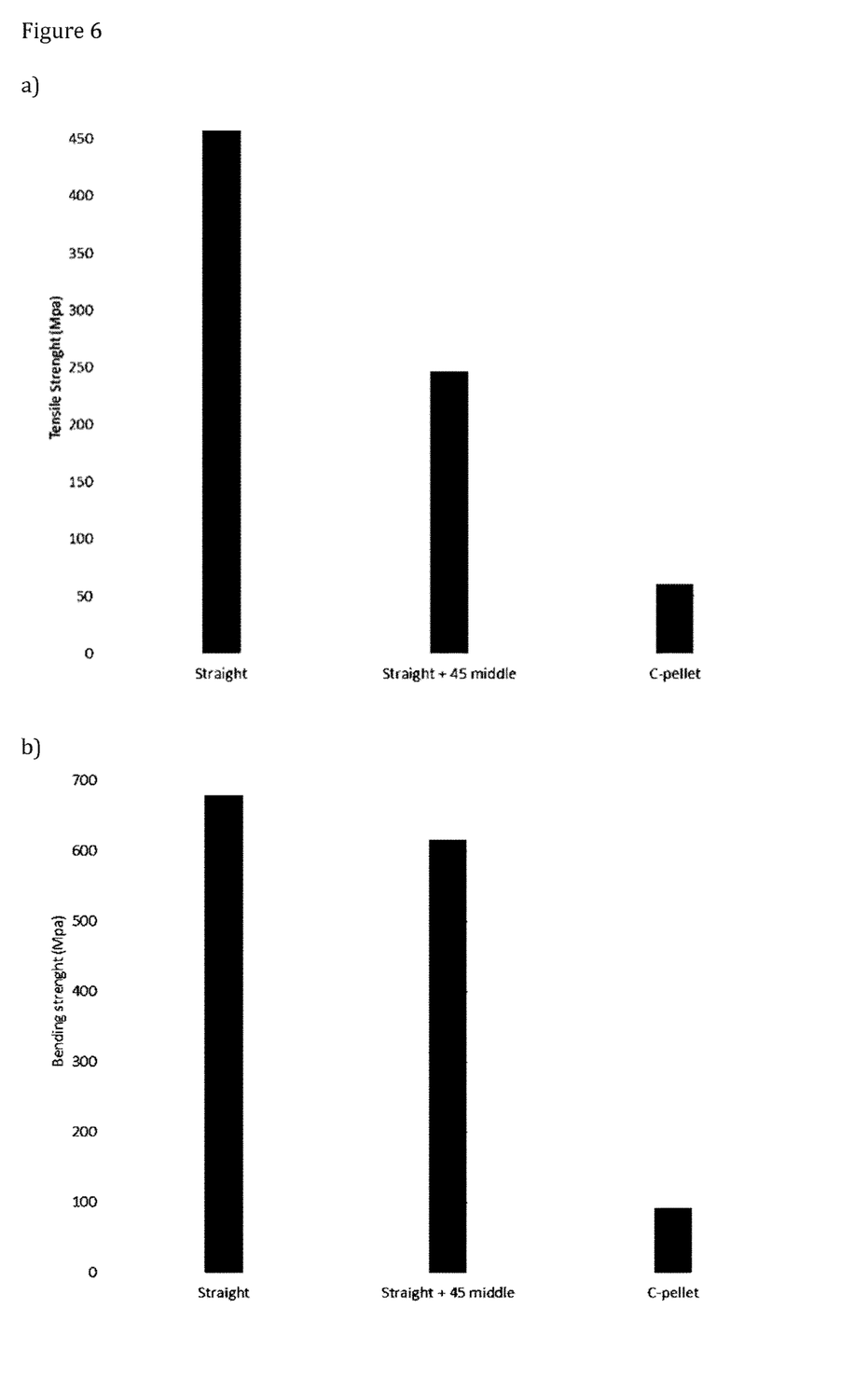
FIG. 6 shows results of mechanical tests of three implant samples.

As can be seen from FIG. 6, Sample 1 (Straight) and Sample 2 (Straight+45 middle) manufactured in accordance with the present invention provide significantly higher tensile strength and bending strength as compared to reference Sample 3 (C-pellet).

Example 2

Complex fiber orientation design was made layer by layer with hand drawing using a software for a distal radius plate. The preform has 10 layers. The preform was printed using a 3D filament printer as shown in FIG. 2. As shown in FIG. 3, the preform was compression molded into the final distal radius plate shape shown in FIG. 4.

Figure 7:
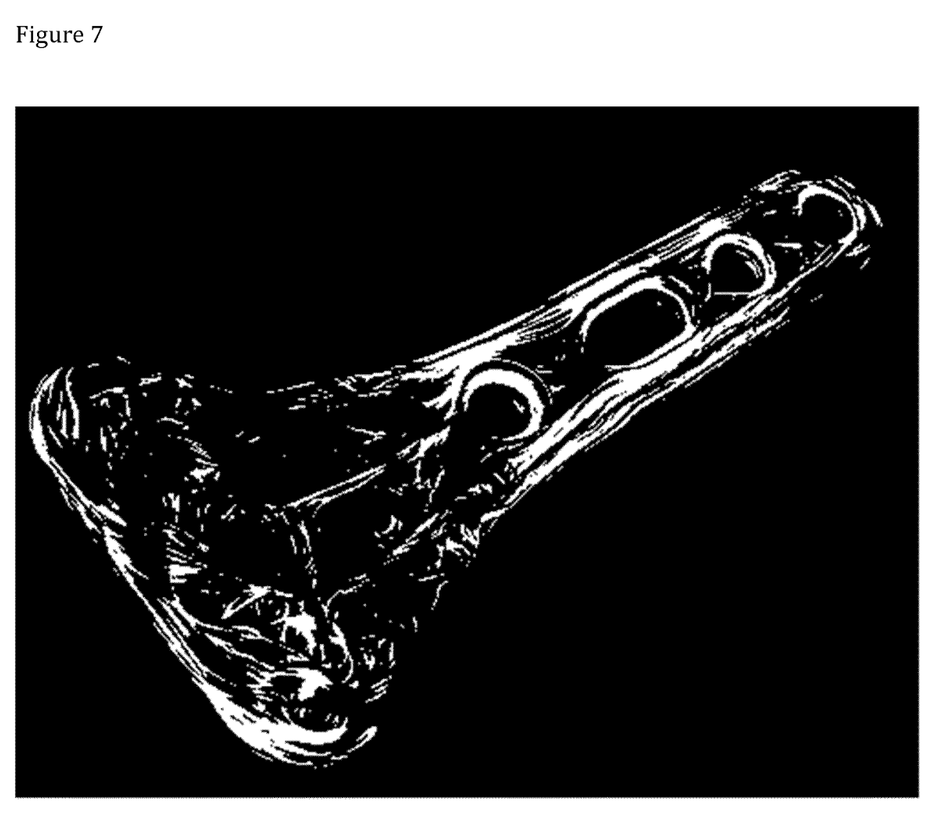
FIGS. 7, 8 and 9 show uCT view of the fiber orientation in a distal radius plate.
Figure 8:
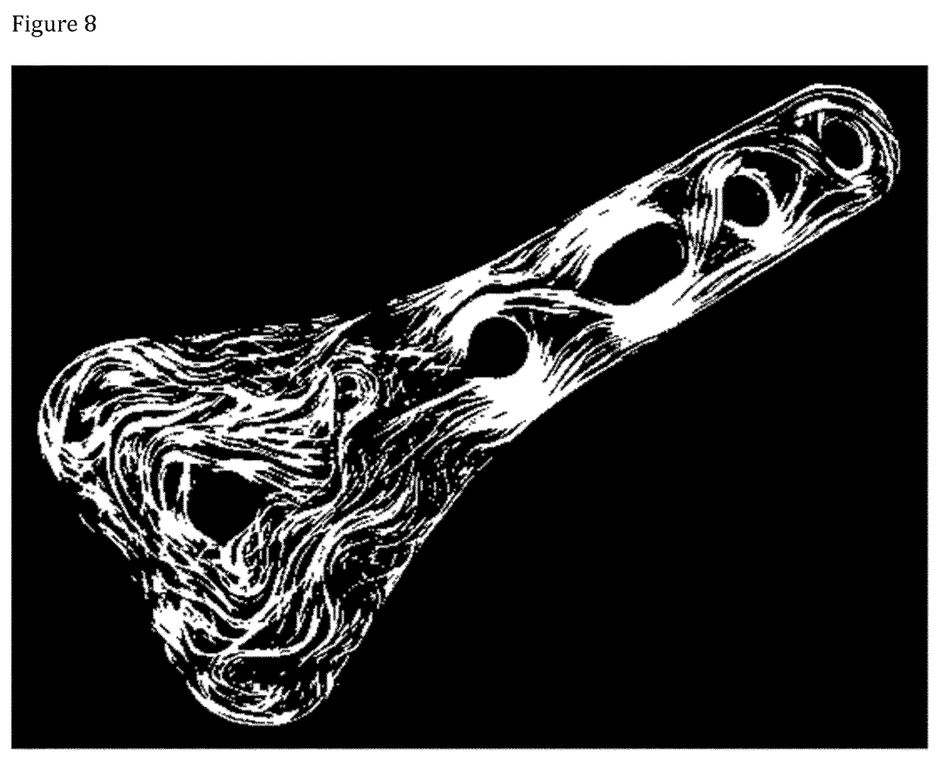
Figure 9:
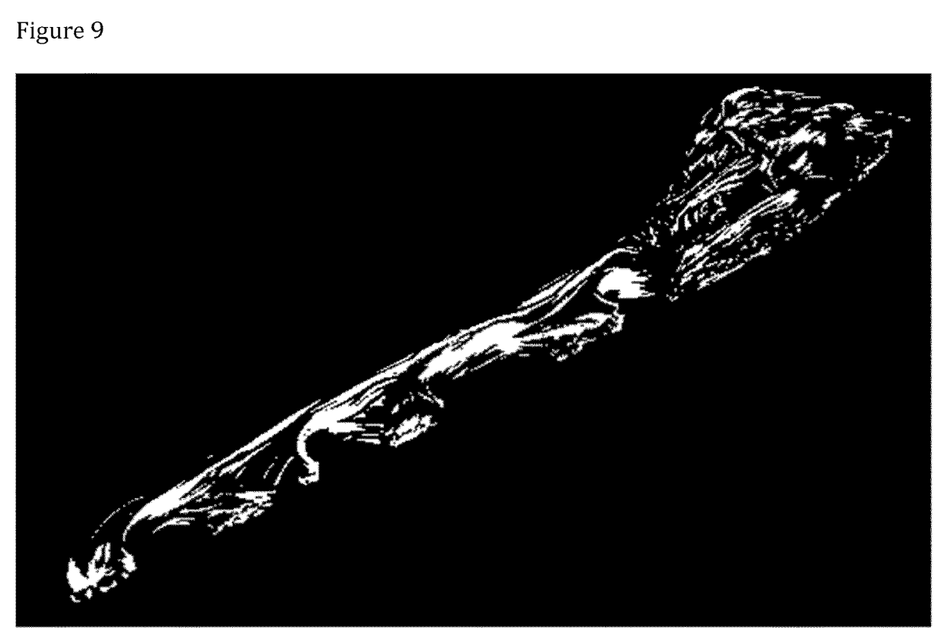

The fiber structure of the final product was inspected using a micro computed tomography (micro-CT). As can be seen in FIGS. 5 to 7 the fiber structure nicely intermingles between the layers.

It will be obvious to a person skilled in the art that, as the technology advances, the inventive concept can be implemented in various ways. The invention and its embodiments are not limited to the examples described above but may vary within the scope of the claims.

The invention claimed is:

1. An orthopedic implant comprising a continuous reinforced composite filament in a freely predetermined fiber orientation in multiple continuous successive layers,
    wherein the continuous reinforced composite filament comprises a bioabsorbable polymer matrix and continuous bioabsorbable reinforcing fibers,
    wherein the continuous bioabsorbable reinforcing fibers of consecutive layers at least partly intermingle and/or intertwine forming a three dimensionally interlocked continuous fiber structure, and
    wherein the continuous bioabsorbable reinforcing fibers are continuous bioabsorbable glass fibers, continuous bioabsorbable ceramic fibers, continuous bioabsorbable mineral fibers, or continuous bioabsorbable cellulosic fibers.

2. The orthopedic implant of claim 1, wherein the implant comprises one or more hole(s), whereby said hole(s) is(are) encircled at least once by the continuous reinforced composite filament.

3. The orthopedic implant of claim 1, wherein the continuous bioabsorbable reinforcing fibers are continuous bioabsorbable glass fibers.

4. The orthopedic implant of claim 1, wherein the orthopedic implant comprises 2 to 200, preferably from 2 to 20, more preferably from 2 to 10, most preferably from 2 to 6 layers of the reinforced composite filament.

5. The orthopedic implant of claim 1, wherein the average filament diameter of the continuous reinforced composite filament is from 0.05 mm to 20 mm, preferably from 0.5 mm to 3.0 mm, more preferably from 0.8 mm to 2.0 mm.

6. The orthopedic implant of claim 1, wherein the average fiber diameter of a single fiber of the continuous reinforcing bioabsorbable fibers is from 1 to 35 µm, preferably from 5 to 30 µm, more preferably from 10 to 15 µm.

7. The orthopedic implant of claim 3, wherein the continuous bioabsorbable glass fibers are melt derived bioabsorbable glass fibers.

8. The orthopedic implant of claim 7, wherein the continuous bioabsorbable reinforcing fibers are melt derived bioabsorbable glass fibers and have a composition in the following weight % ranges (as a percent over the total weight of the glass fiber composition):

| | |
|---|---|
| $SiO_2$ | 40 to 90 wt %, |
| $Na_2O$ | 5 to 30 wt %, |
| $K_2O$ | 0 to 20 wt %, |
| CaO | 5 to 30 wt %, |
| MgO | 0 to 10 wt %, |
| $P_2O_5$ | 0 to 10 mol %, |
| $B_2O_3$ | 0 to 15 wt %, |
| $Al_2O_3$ | 0 to 5 wt %, |
| $CaF_3$ | 0 to 25 wt %, |
| SrO | 0 to 10 wt %, and |
| $Li_2O$ | 0 to 1 wt %. |

9. The orthopedic implant of claim 1, wherein the bioabsorbable polymer matrix is selected from a group consisting of bioabsorbable polyesters, PLLA (poly-L-lactide), PDLLA (poly-DL-lactide), PLDLA, PGA (poly-glycolic acid), PLGA (poly-lactide-glycolic acid), PCL (polycaprolactone), PLLA-PCL and combinations thereof.

10. The orthopedic implant of claim 1, wherein the continuous reinforced composite filament is deposited by a three dimensionally controlled fiber strand feeding machine in a predetermined fiber orientation in continuous successive layers to form a filament preform and the said preform is molded in a mold to form a final shape of the orthopedic implant.

11. The orthopedic implant of claim 1, wherein the filament preform is compression molded in a mold to form the final shape of the orthopedic implant.

12. The orthopedic implant of claim 1, wherein the filament preform is injection molded in a mold to form the final shape of the orthopedic implant.

13. The orthopedic implant of claim 1, wherein the orthopedic implant consists of the reinforced composite filament.

14. The orthopedic implant of claim 1, wherein the continuous bioabsorbable reinforcing fibers are continuous bioabsorbable mineral fibers, and the continuous bioabsorbable mineral fibers are hydroxyapatite fibers, tricalcium phosphate fibers, calcium sulfate fibers, or calcium phosphate fibers.

15. The orthopedic implant of claim 1, wherein the three dimensionally interlocked continuous fiber structure is compression molded at an elevated temperature.

16. The orthopedic implant of claim 1, wherein the continuous bioabsorbable reinforcing fibers continue unbroken at least from one filament layer to the next, and
wherein the continuous bioabsorbable reinforcing fibers of consecutive layers at least partly intermingle and/or intertwine so that successive filament layers formed of the continuous reinforced composite filament merge in forming the three dimensionally interlocked continuous fiber structure.

17. The orthopedic implant of claim 16, wherein the continuous reinforced composite filament has a length at least as long as a maximum dimension of the orthopedic implant.

18. The orthopedic implant of claim 17, wherein the length of continuous reinforced composite filament is such that only one strand thereof is used in forming the orthopedic implant.

19. A method of manufacturing an orthopedic implant, the method comprising
(a) depositing a continuous reinforced composite filament comprising a bioabsorbable polymer matrix and continuous bioabsorbable fibers by a three dimensionally controlled fiber placement device in a freely predetermined fiber orientation in continuous successive layers to form a filament preform, and
(b) molding the filament preform in a mold to obtain a molded product having final shape of the orthopedic implant,
wherein the continuous bioabsorbable reinforcing fibers of consecutive layers at least partly intermingle and/or intertwine forming a three dimensionally interlocked continuous fiber structure, and
wherein the continuous bioabsorbable reinforcing fibers are continuous bioabsorbable glass fibers, continuous bioabsorbable ceramic fibers, continuous bioabsorbable mineral fibers, or continuous bioabsorbable cellulosic fibers.

20. The method as claimed in claim 19, wherein the process further comprises designing the freely predetermined fiber orientation of the filament preform.

21. The method as claimed in claim 19, further comprising surface finishing of the molded product to obtain the orthopedic implant.

22. The method as claimed in claim 19, wherein the continuous filament preform is compression molded in a mold to obtain molded product having final shape of the orthopedic implant.

23. The method as claimed in claim 19, wherein the continuous reinforced composite filament structure is defined layer by layer using free drawing with software.

24. The method as claimed in claim 19, wherein the continuous reinforced composite filament structure is defined layer by layer using a combination of free drawing and computer calculation with software.

25. The method as claimed in claim 19, wherein the continuous reinforced composite filament structure is defined layer by layer using computer calculation with software.

26. A method of repairing a damaged bone comprising introducing the orthopedic implant of claim 1, to the damaged bone.

* * * * *